United States Patent
Zhang et al.

(10) Patent No.: US 12,320,815 B2
(45) Date of Patent: Jun. 3, 2025

(54) COMPOSITIONS AND METHODS FOR ENRICHMENT AND DETECTION OF UBIQUITIN AND UBIQUITIN CONJUGATES

(71) Applicant: YALE UNIVERSITY, New Haven, CT (US)

(72) Inventors: Mengwen Zhang, New Haven, CT (US); Jason Berk, Hamden, CT (US); Mark Hochstrasser, Hamden, CT (US)

(73) Assignee: Yale University, New Haven, CT (US)

( * ) Notice: Subject to any disclaimer, the term of this patent is extended or adjusted under 35 U.S.C. 154(b) by 1191 days.

(21) Appl. No.: 17/061,250

(22) Filed: Oct. 1, 2020

(65) Prior Publication Data
US 2021/0102950 A1    Apr. 8, 2021

Related U.S. Application Data

(60) Provisional application No. 62/909,545, filed on Oct. 2, 2019.

(51) Int. Cl.
*C07K 14/01* (2006.01)
*C07K 14/00* (2006.01)
*C07K 17/02* (2006.01)
*G01N 33/68* (2006.01)

(52) U.S. Cl.
CPC ....... *G01N 33/6842* (2013.01); *C07K 14/001* (2013.01); *C07K 17/02* (2013.01); *G01N 2440/36* (2013.01)

(58) Field of Classification Search
CPC ........... G01N 33/6842; G01N 2440/36; C07K 14/001; C07K 17/02; C07K 14/00; C07K 17/10
See application file for complete search history.

(56) References Cited

PUBLICATIONS

Husnjak et al, Annual Review of Biochemistry, 2012, 81, 291-322. (Year: 2012).*
Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Berk, et al., "Biochemical Characterization of a Deubiquitinase Effector Protein from Orientia tsutsugamushi", American Society for Rickettsiology Conference, Santa Fe, New Mexico, Jun. 11, 2019.
Berk, et al., "Insights into Scrub Typhus: Characterization of a Deubiquitinase Effector Protein from the Pathogenic Bacterium Orientia tsutsugamushi", FASEB Ubiquitin & Cellular Regulation, Snowmass, CO, Jun. 18, 2018.
Hochstrasser, "A deubiquitylase with baggage: A multidomain effector from the pathogenic bacterium Orientia tsutsugamushi", UK Biochemical Society Conference, "Deubiquitylases: from mechanism to physiology" (University of Edinburgh, Scotland, UK), Jun. 19, 2019.

* cited by examiner

*Primary Examiner* — Sudhakar Katakam
(74) *Attorney, Agent, or Firm* — Saul Ewing, LLP; Kathryn Doyle; Domingos Silva

(57) ABSTRACT

Described herein are compositions and methods for detecting the presence of ubiquitination in a sample. The compositions include synthetic peptides containing a high affinity ubiquitin binding domain and an additional peptide sequence that can be coupled to materials such as resins and dyes.

18 Claims, 4 Drawing Sheets
Specification includes a Sequence Listing.

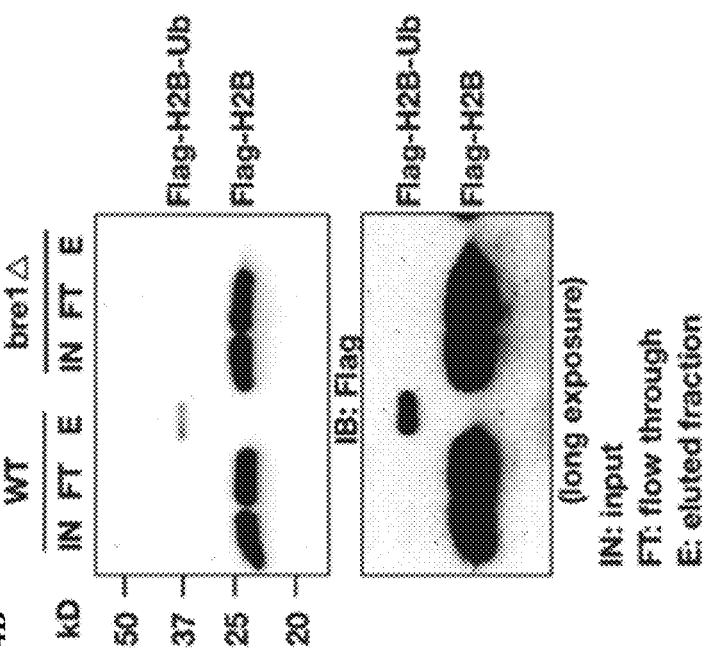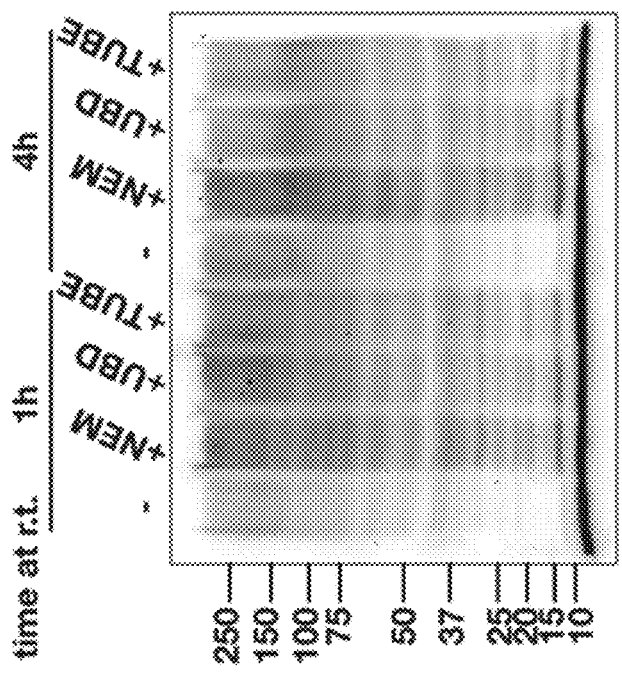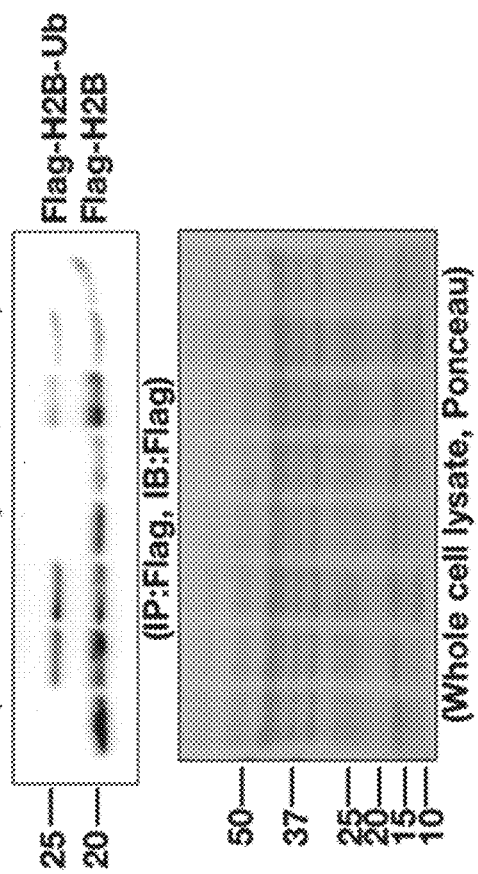
FIG. 4A
FIG. 4B

```
                           SEQUENCE LISTING

<160> NUMBER OF SEQ ID NOS: 9

<210> SEQ ID NO 1
<211> LENGTH: 96
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding
<220> FEATURE:
<221> NAME/KEY: MISC_FEATURE
<222> LOCATION: (1)..(1)
<223> OTHER INFORMATION: Xaa = linker L or (Xaa)n where  Xaa = Ala, Arg,
      Asn, Asp, Cys, Gln, Glu, Gly, His, Ile, Leu, Met, Phe, Pro, Ser,
      Thr, Trp, Tyr, Val, Sec, Penicillamine, Hmy, Se-Met and n = 1 to
      1000

<400> SEQUENCE: 1

Xaa Val Asn Phe Leu Ser Glu Asn Arg Met Ile Thr Ser Ala Ala Ala
1               5                   10                  15

Ala Leu Ala Asp Thr Leu Leu Lys Asn Asn Asn Arg Ile Thr Glu Gly
            20                  25                  30

Val Leu Val Asp Arg Ile Phe Asp Asn Lys Ile Leu Ser Val Gln Glu
        35                  40                  45

Lys Gln Gln Leu Leu Asn Asn Leu Leu Asp Asn His Ile Lys Glu Asn
    50                  55                  60

Lys Ser Leu Thr Lys Glu Ser Leu Thr Arg Met Leu Ala Ser Thr His
65                  70                  75                  80

Phe Val Gln Gln Gln Ala Asn Val Leu Leu Asn Glu Lys Phe Asn Lys
                85                  90                  95

<210> SEQ ID NO 2
<211> LENGTH: 96
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding
<220> FEATURE:
<221> NAME/KEY: MISC_FEATURE
<222> LOCATION: (1)..(1)
<223> OTHER INFORMATION: Xaa = a synthetic linker L or (Xaa)n where
      Xaa = Ala, Arg, Asn, Asp, Cys, Gln, Glu, Gly, His, Ile, Leu, Met,
      Phe, Pro, Ser, Thr, Trp, Tyr, Val, Sec, Penicillamine, Hmy, Se-Met
      and n = 6 and at least 2 Xaa are Cys.

<400> SEQUENCE: 2
```

Xaa Val Asn Phe Leu Ser Glu Asn Arg Met Ile Thr Ser Ala Ala Ala
1               5                   10                  15

Ala Leu Ala Asp Thr Leu Leu Lys Asn Asn Arg Ile Thr Glu Gly
            20                  25                  30

Val Leu Val Asp Arg Ile Phe Asp Asn Lys Ile Leu Ser Val Gln Glu
            35                  40                  45

Lys Gln Gln Leu Leu Asn Asn Leu Leu Asp Asn His Ile Lys Glu Asn
50                  55                  60

Lys Ser Leu Thr Lys Glu Ser Leu Thr Arg Met Leu Ala Ser Thr His
65                  70                  75                  80

Phe Val Gln Gln Gln Ala Asn Val Leu Leu Asn Glu Lys Phe Asn Lys
                85                  90                  95

<210> SEQ ID NO 3
<211> LENGTH: 6
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding

<400> SEQUENCE: 3

Cys Gly Cys Gly Ser Gly
1               5

<210> SEQ ID NO 4
<211> LENGTH: 101
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding

<400> SEQUENCE: 4

Cys Gly Cys Gly Ser Gly Val Asn Phe Leu Ser Glu Asn Arg Met Ile
1               5                   10                  15

Thr Ser Ala Ala Ala Ala Leu Ala Asp Thr Leu Leu Lys Asn Asn
            20                  25                  30

Arg Ile Thr Glu Gly Val Leu Val Asp Arg Ile Phe Asp Asn Lys Ile
            35                  40                  45

Leu Ser Val Gln Glu Lys Gln Gln Leu Leu Asn Asn Leu Leu Asp Asn
50                  55                  60

His Ile Lys Glu Asn Lys Ser Leu Thr Lys Glu Ser Leu Thr Arg Met
65                  70                  75                  80

Leu Ala Ser Thr His Phe Val Gln Gln Gln Ala Asn Val Leu Leu Asn
                85                  90                  95

Glu Lys Phe Asn Lys
            100

<210> SEQ ID NO 5
<211> LENGTH: 143
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding
<220> FEATURE:
<221> NAME/KEY: MISC_FEATURE
<222> LOCATION: (1)..(1)
<223> OTHER INFORMATION: Xaa = linker L or (Xaa)n where  Xaa = Ala, Arg, Asn, Asp, Cys, Gln, Glu, Gly, His, Ile, Leu, Met, Phe, Pro, Ser, Thr, Trp, Tyr, Val, Sec, Penicillamine, Hmy, Se-Met and n = 1 to 1000

<400> SEQUENCE: 5

```
Xaa Val Asn Phe Leu Ser Glu Asn Arg Met Ile Thr Ser Ala Ala Ala
1               5                   10                  15

Ala Leu Ala Asp Thr Leu Leu Lys Asn Asn Asn Arg Ile Thr Glu Gly
            20                  25                  30

Val Leu Val Asp Arg Ile Phe Asp Asn Lys Ile Leu Ser Val Gln Glu
        35                  40                  45

Lys Gln Gln Leu Leu Asn Asn Leu Leu Asp Asn His Ile Lys Glu Asn
    50                  55                  60

Lys Ser Leu Thr Lys Glu Ser Leu Thr Arg Met Leu Ala Ser Thr His
65                  70                  75                  80

Phe Val Gln Gln Gln Ala Asn Val Leu Leu Asn Glu Lys Phe Asn Lys
                85                  90                  95

Ser Thr Ala Asn Leu Gln Ala Ser Asn Ala Ser Ala Glu Val Ser Ser
            100                 105                 110

Lys Glu Glu Leu Tyr Val Pro Lys Ile Asn Gln Val Glu Glu Ser Leu
        115                 120                 125

Glu Ala Gln Leu Lys Tyr Ile Asn Glu His Ile Ala Ser Gln Leu
    130                 135                 140
```

<210> SEQ ID NO 6
<211> LENGTH: 148
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding

<400> SEQUENCE: 6

```
Cys Gly Cys Gly Ser Gly Val Asn Phe Leu Ser Glu Asn Arg Met Ile
1               5                   10                  15

Thr Ser Ala Ala Ala Leu Ala Asp Thr Leu Leu Lys Asn Asn Asn
            20                  25                  30

Arg Ile Thr Glu Gly Val Leu Val Asp Arg Ile Phe Asp Asn Lys Ile
        35                  40                  45

Leu Ser Val Gln Glu Lys Gln Gln Leu Leu Asn Asn Leu Leu Asp Asn
    50                  55                  60

His Ile Lys Glu Asn Lys Ser Leu Thr Lys Glu Ser Leu Thr Arg Met
65                  70                  75                  80

Leu Ala Ser Thr His Phe Val Gln Gln Gln Ala Asn Val Leu Leu Asn
                85                  90                  95

Glu Lys Phe Asn Lys Ser Thr Ala Asn Leu Gln Ala Ser Asn Ala Ser
            100                 105                 110

Ala Glu Val Ser Ser Lys Glu Glu Leu Tyr Val Pro Lys Ile Asn Gln
        115                 120                 125

Val Glu Glu Ser Leu Glu Ala Gln Leu Lys Tyr Ile Asn Glu His Ile
    130                 135                 140

Ala Ser Gln Leu
145
```

<210> SEQ ID NO 7
<211> LENGTH: 397
<212> TYPE: PRT

<213> ORGANISM: Artificial Sequence
<220> FEATURE:
<223> OTHER INFORMATION: Peptide
<220> FEATURE:
<223> OTHER INFORMATION: Ubiquitin Binding

<400> SEQUENCE: 7

```
His Met Cys Gly Cys Gly Ser Gly Val Asn Phe Leu Ser Glu Asn Arg
1               5                   10                  15

Met Ile Thr Ser Ala Ala Ala Leu Ala Asp Thr Leu Leu Lys Asn
            20                  25                  30

Asn Asn Arg Ile Thr Glu Gly Val Leu Val Asp Arg Ile Phe Asp Asn
            35                  40                  45

Lys Ile Leu Ser Val Gln Glu Lys Gln Gln Leu Leu Asn Asn Leu Leu
    50                  55                  60

Asp Asn His Ile Lys Glu Asn Lys Ser Leu Thr Lys Glu Ser Leu Thr
65                  70                  75                  80

Arg Met Leu Ala Ser Thr His Phe Val Gln Gln Gln Ala Asn Val Leu
                85                  90                  95

Leu Asn Glu Lys Phe Asn Lys Gly Ser Gly Val Asn Phe Leu Ser Glu
            100                 105                 110

Asn Arg Met Ile Thr Ser Ala Ala Ala Leu Ala Asp Thr Leu Leu
            115                 120                 125

Lys Asn Asn Asn Arg Ile Thr Glu Gly Val Leu Val Asp Arg Ile Phe
130                 135                 140

Asp Asn Lys Ile Leu Ser Val Gln Glu Lys Gln Gln Leu Leu Asn Asn
145                 150                 155                 160

Leu Leu Asp Asn His Ile Lys Glu Asn Lys Ser Leu Thr Lys Glu Ser
                165                 170                 175

Leu Thr Arg Met Leu Ala Ser Thr His Phe Val Gln Gln Gln Ala Asn
            180                 185                 190

Val Leu Leu Asn Glu Lys Phe Asn Lys Gly Ser Gly Val Asn Phe Leu
            195                 200                 205

Ser Glu Asn Arg Met Ile Thr Ser Ala Ala Ala Leu Ala Asp Thr
210                 215                 220

Leu Leu Lys Asn Asn Asn Arg Ile Thr Glu Gly Val Leu Val Asp Arg
225                 230                 235                 240

Ile Phe Asp Asn Lys Ile Leu Ser Val Gln Glu Lys Gln Gln Leu Leu
                245                 250                 255

Asn Asn Leu Leu Asp Asn His Ile Lys Glu Asn Lys Ser Leu Thr Lys
            260                 265                 270

Glu Ser Leu Thr Arg Met Leu Ala Ser Thr His Phe Val Gln Gln Gln
            275                 280                 285

Ala Asn Val Leu Leu Asn Glu Lys Phe Asn Lys Gly Ser Gly Val Asn
            290                 295                 300

Phe Leu Ser Glu Asn Arg Met Ile Thr Ser Ala Ala Ala Leu Ala
305                 310                 315                 320

Asp Thr Leu Leu Lys Asn Asn Asn Arg Ile Thr Glu Gly Val Leu Val
                325                 330                 335

Asp Arg Ile Phe Asp Asn Lys Ile Leu Ser Val Gln Glu Lys Gln Gln
            340                 345                 350

Leu Leu Asn Asn Leu Leu Asp Asn His Ile Lys Glu Asn Lys Ser Leu
            355                 360                 365

Thr Lys Glu Ser Leu Thr Arg Met Leu Ala Ser Thr His Phe Val Gln
370                 375                 380
```

Gln Gln Ala Asn Val Leu Leu Asn Glu Lys Phe Asn Lys
385             390                 395

<210> SEQ ID NO 8
<211> LENGTH: 1200
<212> TYPE: DNA
<213> ORGANISM: Artificial Sequence
<220> FEATURE:
<223> OTHER INFORMATION: Peptide
<220> FEATURE:
<223> OTHER INFORMATION: Ubiquitin Binding

<400> SEQUENCE: 8

| | | | | | |
|---|---|---|---|---|---|
| catatgtgtg | gatgtggatc | aggagttaat | ttcctgagcg | aaaacagaat | gattacctct | 60 |
| gccgctgcag | ccttggctga | tactttgctg | aagaacaaca | acagaatcac | agagggtgtg | 120 |
| ctggttgata | gaatcttcga | caataagatt | ttgtccgtgc | aggaaaaaca | gcaattgctg | 180 |
| aacaatttgc | tggacaacca | tattaaggaa | aacaaatctc | tgactaaaga | gtccctgaca | 240 |
| agaatgttgg | cttctaccca | ctttgttcag | caacaggcaa | acgtgttgct | gaatgagaag | 300 |
| ttcaacaaag | gatcaggagt | taatttcctg | agcgaaaaca | gaatgattac | ctctgccgct | 360 |
| gcagccttgg | ctgatacttt | gctgaagaac | aacaacagaa | tcacagaggg | tgtgctggtt | 420 |
| gatagaatct | tcgacaataa | gatttttgtcc | gtgcaggaaa | acagcaatt | gctgaacaat | 480 |
| ttgctggaca | accatattaa | ggaaaacaaa | tctctgacta | agagtccct | gacaagaatg | 540 |
| ttggcttcta | cccactttgt | tcagcaacag | gcaaacgtgt | tgctgaatga | aagttcaac | 600 |
| aaaggatcag | gagttaattt | cctgagcgaa | aacagaatga | ttacctctgc | cgctgcagcc | 660 |
| ttggctgata | ctttgctgaa | gaacaacaac | agaatcacag | agggtgtgct | ggttgataga | 720 |
| atcttcgaca | ataagatttt | gtccgtgcag | gaaaaacagc | aattgctgaa | caatttgctg | 780 |
| gacaaccata | ttaaggaaaa | caaatctctg | actaaagagt | ccctgacaag | aatgttggct | 840 |
| tctacccact | ttgttcagca | acaggcaaac | gtgttgctga | atgagaagtt | caacaagga | 900 |
| tcaggagtta | atttcctgag | cgaaaacaga | atgattacct | ctgccgctgc | agccttggct | 960 |
| gatactttgc | tgaagaacaa | caacagaatc | acagagggtg | tgctggttga | tagaatcttc | 1020 |
| gacaataaga | ttttgtccgt | gcaggaaaaa | cagcaattgc | tgaacaattt | gctggacaac | 1080 |
| catattaagg | aaaacaaatc | tctgactaaa | gagtccctga | caagaatgtt | ggcttctacc | 1140 |
| cactttgttc | agcaacaggc | aaacgtgttg | ctgaatgaga | agttcaacaa | atagggatcc | 1200 |

<210> SEQ ID NO 9
<211> LENGTH: 96
<212> TYPE: PRT
<213> ORGANISM: Artificial Sequence
<220> FEATURE:
<223> OTHER INFORMATION: Peptide
<220> FEATURE:
<223> OTHER INFORMATION: Ubiquitin Binding
<220> FEATURE:
<221> NAME/KEY: MISC_FEATURE
<222> LOCATION: (1)..(1)
<223> OTHER INFORMATION: Xaa = a synthetic linker L or (Xaa)n where
      Xaa = Ala, Arg, Asn, Asp, Cys, Gln, Glu, Gly, His, Ile, Leu, Met,
      Phe, Pro, Ser, Thr, Trp, Tyr, Val, Sec, Penicillamine, Hmy, Se-Met
      and n = 6 and at least 2 Xaa are Cys.
<220> FEATURE:
<221> NAME/KEY: MISC_FEATURE
<222> LOCATION: (1)..(96)
<223> OTHER INFORMATION: Peptide conjugated to Cy5-maleimide

<400> SEQUENCE: 9

-continued

```
Xaa Val Asn Phe Leu Ser Glu Asn Arg Met Ile Thr Ser Ala Ala Ala
1             5               10              15

Ala Leu Ala Asp Thr Leu Leu Lys Asn Asn Arg Ile Thr Glu Gly
        20              25              30

Val Leu Val Asp Arg Ile Phe Asp Asn Lys Ile Leu Ser Val Gln Glu
        35              40              45

Lys Gln Gln Leu Leu Asn Asn Leu Leu Asp Asn His Ile Lys Glu Asn
    50              55              60

Lys Ser Leu Thr Lys Glu Ser Leu Thr Arg Met Leu Ala Ser Thr His
65              70              75              80

Phe Val Gln Gln Gln Ala Asn Val Leu Leu Asn Glu Lys Phe Asn Lys
            85              90              95
```

COMPOSITIONS AND METHODS FOR ENRICHMENT AND DETECTION OF UBIQUITIN AND UBIQUITIN CONJUGATES

CROSS-REFERENCE TO RELATED APPLICATION

This application claims priority to U.S. Provisional Patent Application Ser. No. 62/909,545 entitled "COMPOSITIONS AND METHODS FOR ENRICHMENT AND DETECTION OF UBIQUITIN AND UBIQUITIN CONJUGATES," filed Oct. 2, 2019, the disclosure of which is incorporated herein by reference in its entirety.

STATEMENT REGARDING FEDERALLY SPONSORED RESEARCH

This invention was made with government support under GM053756 and GM046904, awarded by the National Institutes of Health. The government has certain rights in this invention.

INCORPORATION-BY-REFERENCE OF MATERIAL SUBMITTED AS A TEXT FILE VIA THE OFFICE ELECTRONIC FILING SYSTEM

This invention contains one or more sequences in a computer readable format in an accompanying text file titled "Sequence Listing," the contents of which are incorporated herein by reference in their entirety. The text file is about 16 KB, was created on Oct. 1, 2020, and is being submitted electronically via EFS-Web

BACKGROUND

Ubiquitin is an essential eukaryotic post-translational modification (PTM) with critical roles in targeted protein degradation, autophagy, DNA repair, and endocytosis among other cellular functions. Identification of ubiquitinated proteins and the site of modification is critical for better understanding the use of this PTM in various biological pathways. Many ubiquitinome-enriching tools exist but are engineered for poly-ubiquitin chain recognition.

There are two frequently encountered challenges in the ubiquitin research field: 1) enriching monoubiquitinated substrates as well as ubiquitin polymers with any one of seven different ubiquitin chain linkages, and 2) the ability to detect ubiquitinated proteins with high specificity and to do so cheaply and with an infinitely renewable reagent, which is not the case for most antibodies.

There is therefore a market need for tools capable of enriching mono-ubiquitinated substrates as well as reagents that can enrich different ubiquitin chain linkages in an unbiased fashion. The present invention addresses these needs.

BRIEF SUMMARY OF THE INVENTION

Provided herein is an ubiquitin-binding peptide comprising the sequence of SEQ ID NO: 1 or SEQ ID NO:5, wherein Z is $(X_{aa})_n$ or L, wherein each $X_{aa}$ is independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, penicillamine, homocysteine, and selenomethionine, provided that at least one $X_{aa}$ is selected from the group consisting of cysteine, selenocysteine, penicillamine, homocysteine, methionine, and selenomethionine, wherein L is a chemical moiety comprising from 1 to 500 atoms selected from the group consisting of C, N, O, S, P, H, F, Cl, and Br, and wherein n is an integer from 1 to 1000.

Also provided herein are a method of detecting the presence of a ubiquitinated substance. In certain embodiments, the method comprises contacting a sample comprising at least one ubiquitinated substance with the ubiquitin-binding peptides described herein, and detecting in the sample the presence of the ubiquitin-binding peptide bound to the at least one ubiquitinated sub stance.

BRIEF DESCRIPTION OF THE FIGURES

The drawings illustrate generally, by way of example, but not by way of limitation, various embodiments of the present application.

FIGS. 4A-4B show protection and enrichment of monoubiquitylated histone H2B with UBD. FIG. 4A shows that both UBD and TUBE were able to protect the bulk of ubiquitylated proteins in yeast whole cell lysate while only UBD but not TUBE was able to protect mono-ubiquitylated histone H2B. FIG. 4B illustrates that SULFOLINK® resin with immobilized UBD was able to affinity-purify monoubiquitylated Flag-H2B.

DETAILED DESCRIPTION OF THE INVENTION

Figure 1:
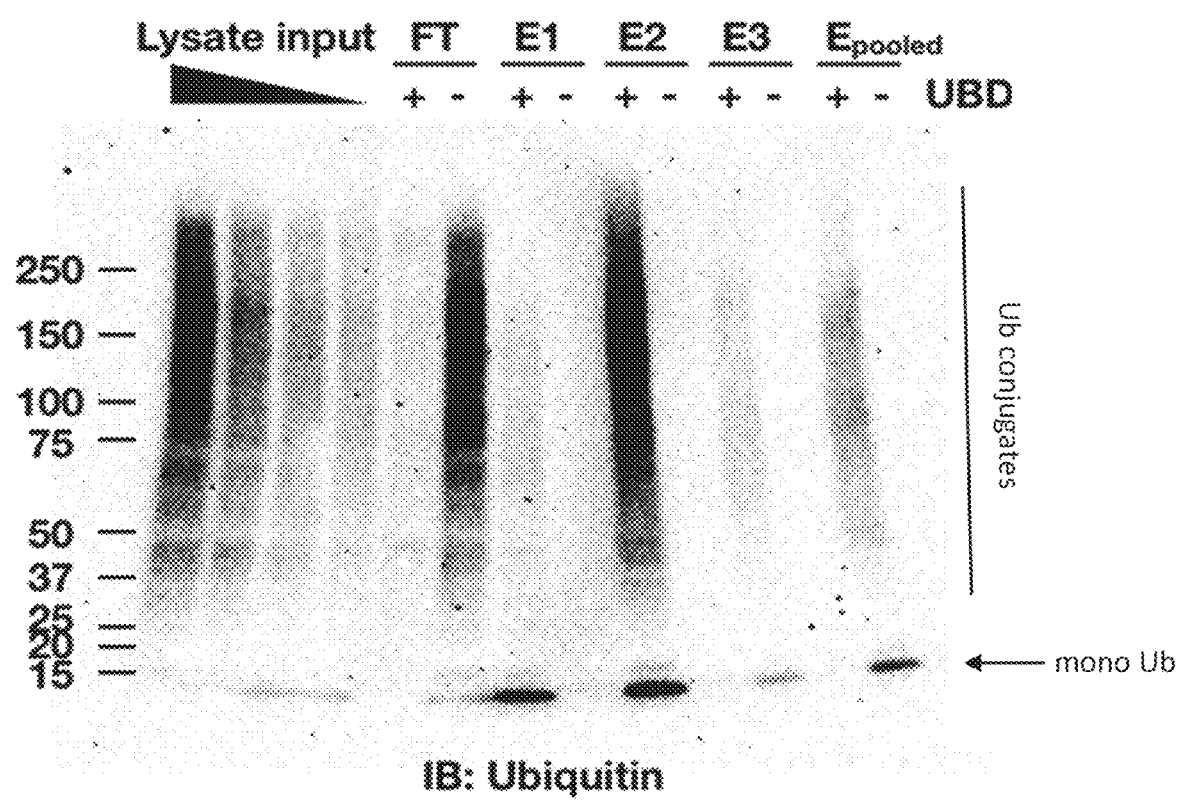
FIG. 1 illustrates ubiquitinome enrichment from yeast lysates by OtUBD (Ot ubiquitin binding domain). Protein inputs, flow through (FT) and elutions (E1-E3,$E_{pooled}$) from a OtUBD-resin binding assay were resolved by SDS-PAGE and immunoblotted for ubiquitin. The negative control (−UBD) is a cysteine modified 'empty' SULFOLINK® resin.

Generating highly sensitive and specific anti-ubiquitin antibodies has been an ongoing challenge in the ubiquitin-proteasome field. One difficulty in producing an effective antibody lies in the extremely high sequence identity and structural similarity of ubiquitin among eukaryotes, which in turn often elicits poor immune responses in the animals. Additionally, antibodies are expensive to generate, polyclonal antibodies have finite supplies, and monoclonal antibodies are rarely purified from ascites fluid anymore (due to concerns about the ethical treatment of animals), resulting in poor titers and reduced sensitivity. The present disclosure provides ubiquitin-binding peptides that can, in some embodiments, solve all of the aforementioned problems. Advantageously, in certain embodiments, the ubiquitin-binding peptides described herein can be economically produced as a recombinant protein with high yields. Surprisingly, in various embodiments, the presence of N-terminal cysteines in the ubiquitin-binding peptides allows for conjugation of different detection moieties (e.g., dyes) without compromising the binding activity of the UBD (ubiquitin binding domain). Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=C=CCH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, 4,5-epoxypentyl, epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl)ethyl, 2-(4-methyl-3,4-epoxycyciohexyl)propyl, 2-(3,4-epoxy-3-methylcylohexyl)-2-methylethyl, and 5,6-epoxyhexyl.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

As used herein, the term "composition" or "pharmaceutical composition" refers to a mixture of at least one compound described herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect (E max) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

Ubiquitin-Binding Peptides

Ubiquitin is a 76-residue polypeptide that is covalently conjugated to target proteins by an enzymatic cascade. In an ATP-dependent manner, an E1 activating enzyme, an E2 conjugating enzyme, and an E3 ligase work successively to attach ubiquitin to a substrate protein. Substrates are modified through a bond formed between the terminal ubiquitin glycine residue and a substrate residue (typically lysine) side chain. Through iterative rounds of ubiquitination, ubiquitin polymers are formed whereby they are linked to each other via any of the seven lysines in ubiquitin or through the N-terminal methionine amino group. The addition of monoubiquitin or polyubiquitin chains to a substrate acts as signal for downstream events. The most well-studied signal is the Lys48-linked chain, which is the predominant targeting signal for proteasome-based substrate degradation.

While much attention has focused on ubiquitin chains, mono-ubiquitination is also a well-established signaling cue. Mono-ubiquitin has been shown to be important for epigenetic regulation (histone modification), transcriptional regulation (p53 and IRF-1), endocytic regulation (epsin proteins), and general protein localization and activation. Given the growing number of examples where monoubiquitin is dictating pathway activity, researchers need methods for the enrichment and detection of novel monoubiquitin sites. In order to capture these proteins along with poly-ubiquitinated substrates, a new ubiquitinome enrichment tool was developed.

Described herein is the highest affinity ubiquitin-binding domain ever reported. The high affinity to mono-ubiquitin makes the ubiquitin-binding peptide described herein a powerful tool for ubiquitin enrichment and detection.

In some embodiments, the ubiquitin-binding peptide has the sequence of SEQ ID NO: 1:

```
                                        (SEQ ID NO: 1)
ZVNFLSENRIMITSAAAALADTLLKNNNRITEGVLVDRIFDNKILSVQEK

QQLLNNLLDNHIKENKSLTKESLTRNILASTHFVQQQANVLLNEKFNK.
```

In the peptide of SEQ ID NO: 1, Z is a synthetic linker L or $(X_{aa})_n$. When Z is $(X_{aa})_n$ each occurrence of $X_{aa}$ is independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, penicillamine, homocysteine, methionine, and selenomethionine, and provided that at least one $X_{aa}$ is selected from the group consisting of cysteine, selenocysteine, penicillamine, homocysteine, and selenomethionine. The peptide of SEQ ID NO: 1 is derived from the ubiquitin binding domain (OtUBD) of an effector protein in the pathogenic bacterium *Orientia tsutsugamushi* (NCBI accession number WP 012462337.1). In various embodiments, Z is located at the N-terminal end of SEQ ID NO: 1. In other embodiments, Z is located at the C-terminal end of SEQ ID NO: 1.

Variable 'n' is an integer from 1 to 1000. When Z is $(X_{aa})_n$, Z can be a peptide, peptide fragment, or a sequence of amino acids or amino acid analogs. In various embodiments, n is 1, 2, 3, 4, 5, 6, 7, 8, 9, 10, 15, 20, 25, 30, 35, 40, 45, 50, 55, 60, 65, 70, 75, 80, 85, 90, 100, 200, 300, 400, 500, 600, 700, 800, 900, or 1000. When Z is $(X_{aa})_n$, the primary, secondary, or tertiary structure of Z can be any structure that does not significantly affect the binding activity of the peptide of SEQ ID NO: 1. By "does not significantly affect the binding activity" it is meant that the ubiquitin binding affinity of the peptide of SEQ ID NO: 1 is not less than about 50%, 55%, 60%, 65%, 70%, 75%, 80%, 85%, 90%, 95%, or 98% of the binding affinity of the native unmodified ubiquitin-binding domain OtUBD, that is, when Z is absent.

Isothermal titration calorimetry was used to determine the binding affinity of the OtUBD for ubiquitin. In various embodiments, the binding affinity ($K_D$) of the peptide of SEQ ID NO: 1 to a single molecule of ubiquitin is about 1 nM to about 50 nM, about 3 nM to about 40 nM, about 5 nM to about 30 nM, or about 10 nM to about 20 nM. In various embodiments, the binding affinity ($K_D$) of the peptide of SEQ ID NO: 1 to a single molecule of ubiquitin is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nM. In some embodiments, a single OtUBD molecule is capable of binding one ubiquitin with an affinity of $K_D$=5.3±3.9 nM. By comparison, the highest affinity UBD found in the literature has a $K_D$ of 2.82 µM (~500-fold weaker binding); this UBD is in isopeptidase T (USP5). The OtUBD is also capable of binding Lys63 or Lys48 di-ubiquitin at a ratio of two UBD molecules to one di-ubiquitin at sub-nanomolar affinity, suggesting the UBD can indiscriminately enrich multiple ubiquitin chain-linkage types. In addition to its high affinity for ubiquitin, OtUBD is well expressed in *E. coli*, easily purified, and stable in 4° C. storage without losing its ubiquitin-binding capacity.

In various embodiments, the ubiquitin-binding peptide has a sequence of SEQ ID NO: 2, wherein variable 'n' is 6 and at least two $X_{aa}$ in Z are cysteine. The peptide of SEQ ID NO: 2 advantageously includes two N-terminal cysteine residues not present in the naturally occurring ubiquitin-binding domain (OtUBD). These N-terminal cysteines allow for the use of thiol chemistry to attach the peptide of SEQ ID NO: 2 to various materials. In various embodiments, the peptide of SEQ ID NO: 2 can be covalently conjugated to SULFOLINK® resin and to Cy5-maleimide, for enrichment and detection of ubiquitinated proteins, respectively.

In certain embodiments, Z is CGCGSG (SEQ ID NO: 3) and the ubiquitin-binding peptide has a sequence of SEQ ID NO: 4:

(SEQ ID NO: 4)
CGCGSGVNFLSENRMITSAAAALADTLLKNNNRITEGVLVDRIFDNKIL

SVQEKQQLLNNLLDNHIKENKSLTKESLTRMLASTHFVQQQANVLLNEK

FNK.

In certain embodiments, the ubiquitin-binding peptide has the sequence of SEQ ID NO: 5:

(SEQ ID NO: 5)
ZVNFLSENRMITSAAAALADTLLKNNNRITEGVLVDRIFDNKILSVQEKQ

QLLNNLLDNHIKENKSLTKESLTRMLASTHFVQQQANVLLNEKFNKSTAN

LQASNASAEVSSKEELYVPKINQVEESLEAQLKYINEHIASQL, where Z is as defined herein. The peptide of SEQ ID NO: 5 has, in certain embodiments, equivalent binding affinity to ubiquitin as the peptide of SEQ ID NO: 1, 2, or 4.

In certain embodiments, the ubiquitin binding peptide has the sequence of SEQ ID NO: 6:

(SEQ ID NO: 6)
CGCGSGVNFLSENRMITSAAAALADTLLKNNNRITEGVLVDRIFDNKILS

VQEKQQLLNNLLDNHIKENKSLTKESLTRMLASTHFVQQQANVLLNEKFN

KSTANLQASNASAEVSSKEELYVPKINQVEESLEAQLKYINEHIASQL.

In some embodiments, when Z is synthetic linker L, L is a chemical moiety that provides spatial separation between the ubiquitin-binding peptide and the substance or substrate attached to the other end of the linker. The nature of the linker L is not particularly limited, and L can contain from 1 to 500 atoms selected from the group consisting of C, N, O, S, P, H, F, Cl, and Br. In various embodiments, L is a chemically stable moiety that does not undergo degradation under any of the conditions described herein and/or that be used in the ubiquitin-binding peptide for any suitable analytical conditions the ubiquitin-binding peptide might be subjected or exposed to. Suitable examples of linkers include, but are not limited to, beta-alanine, 4-aminobutyric acid, 2-aminoethoxyl acetic acid, 5-aminovaleric acid, 6-aminohexanoic acid, and the like. In some embodiments, L can contain from 1 to 30 PEG (polyethylene glycol) units. For example, suitable PEG derivatives include 8-amino-3,6-dioxaoctanoic acid, 12-amino-4,7,10-trioxadodecanoic acid, 15-amino-4,7,10,13-tetraoxapenta-decanoic acid, trioxatridecan-succinamic acid, and the like. In some embodiments, L includes 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 PEG units. Other types of linkers with moieties such as azides, propargyl, and NHS esters can be used, including without limitation 11-azido-3,6,9-trioxaundecanoic acid, 2-[2-(2-propyn-1-yloxy)ethoxy]ethanoic acid, 4,7,10,13,16-pentaoxanonadecanedioic acid di(N-succinimidyl) ester, and the like. In some embodiments, L can connect to the ubiquitin-binding peptide through an amide, ester, ether, carbamate, thioamide, thiourea, carboxylate, or carbonate moiety in L. Linker L can include any of the organic groups described herein. Linkers such as beta-alanine, 4-aminobutyric acid, 2-aminoethoxyl acetic acid, 5-aminovaleric acid, 6-aminohexanoic acid can be attached to the ubiquitin-binding peptide through either through the amino portion or the carboxylic acid portion of the linker. Any of the linker groups described here can be optionally substituted with one or more organic groups described herein. The end of L not attached to the ubiquitin-binding peptide can be attached to another substrate such as, without limitation, a resin, a chemically modified surface that can react with L, a dye, a nucleic acid, an antibody, an antibody fragment, biotin, proteasome inhibitor/modifiers, nanoparticles (e.g., gold nanoparticles, nanotubes, and the like), or an enzyme (e.g., horseradish peroxidase (HRP) or luciferase), and the like. In some embodiments linker L is a chemically cleavable linker, such as a hydrazone.

Preparation of Ubiquitin Binding Peptides

The peptides described herein can be prepared by the general schemes described herein in the Examples, using the synthetic methods known by those skilled in the art.

In various embodiments, a tandem UBD (ubiquitin binding domain) peptide used to produce the ubiquitin-binding peptides described herein has the sequence of SEQ ID NO: 7:

```
                                        (SEQ ID NO: 7)
HMCGCGSGVNFLSENRMITSAAAALADTLLKNNNRITEGVLVDRIFDNKI

LSVQEKQQLLNNLLDNHIKENKSLTKESLTRMLASTHFVQQQANVLLNEK

FNKGSGVNFLSENIMITSAAAALADTLLKNNNRITEGVLVDRIFDNKILS

VQEKQQLLNNLLDNHIKENKSLTKESLTRMLASTHFVQQQANVLLNEKFN

KGSGVNFLSENRMITSAAAALADTLLKNNNRITEGVLVDRIFDNKILSVQ

EKQQLLNNLLDNHIKENKSLTKESLTRMLASTHFVQQQANVLLNEKFNKG

SGVNFLSENRMITSAAAALADTLLKNNNRITEGVLVDRIFDNKILSVQEK

QQLLNNLLDNHIKENKSLTKESLTRMLASTHFVQQQANVLLNEKFNK.
```

The DNA sequence corresponding to the peptide of SEQ ID NO:6 is, in some embodiments, the nucleic acid of SEQ ID NO: 8:

```
                                        (SEQ ID NO: 8)
CATATGTGTGGATGTGGATCAGGAGTTAATTTCCTGAGCGAAAACAGAA

TGATTACCTCTGCCGCTGCAGCCTTGGCTGATACTTTGCTGAAGAACAA

CAACAGAATCACAGAGGGTGTGCTGGTTGATAGAATCTTCGACAATAAG

ATTTTGTCCGTGCAGGAAAAACAGCAATTGCTGAACAATTTGCTGGACA

ACCATATTAAGGAAAACAAATCTCTGACTAAAGAGTCCCTGACAAGAAT

GTTGGCTTCTACCCACTTTGTTCAGCAACAGGCAAACGTGTTGCTGAAT

GAGAAGTTCAACAAAGGATCAGGAGTTAATTTCCTGAGCGAAAACAGAA

TGATTACCTCTGCCGCTGCAGCCTTGGCTGATACTTTGCTGAAGAACAA

CAACAGAATCACAGAGGGTGTGCTGGTTGATAGAATCTTCGACAATAAG

ATTTTGTCCGTGCAGGAAAAACAGCAATTGCTGAACAATTTGCTGGACA

ACCATATTAAGGAAAACAAATCTCTGACTAAAGAGTCCCTGACAAGAAT

GTTGGCTTCTACCCACTTTGTTCAGCAACAGGCAAACGTGTTGCTGAAT

GAGAAGTTCAACAAAGGATCAGGAGTTAATTTCCTGAGCGAAAACAGAA

TGATTACCTCTGCCGCTGCAGCCTTGGCTGATACTTTGCTGAAGAACAA

CAACAGAATCACAGAGGGTGTGCTGGTTGATAGAATCTTCGACAATAAG

ATTTTGTCCGTGCAGGAAAAACAGCAATTGCTGAACAATTTGCTGGACA

ACCATATTAAGGAAAACAAATCTCTGACTAAAGAGTCCCTGACAAGAAT

GTTGGCTTCTACCCACTTTGTTCAGCAACAGGCAAACGTGTTGCTGAAT

GAGAAGTTCAACAAATAGGGATCC.
```

In one embodiment, the nucleic acid sequence of SEQ ID NO: 8 is cloned into two different vectors: pMAL-c5x and a modified form of pET42b comprising 6His-MBP-TEV site. Once these are cloned with the nucleic acid of SEQ ID NO: 8, a stop codon is inserted after the first UBD repeat to generate the UBD peptides described herein.

The peptides described herein also include isotopically-labeled amino acids wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$ is useful in Positron Emission Topography (PET) studies for examining substrate receptor occupancy. Isotopically-labeled amino acids are prepared by any suitable method or by processes using an appropriate isotopically-labeled reagent in place of the non-labeled reagent otherwise employed.

In certain embodiments, the peptides described herein are labeled by other means, including, but not limited to, the use of chromophores or fluorescent moieties, bioluminescent labels, or chemiluminescent labels.

In certain embodiments, reactive functional groups, such as hydroxyl, amino, imino, thio or carboxy groups on the peptides described herein, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

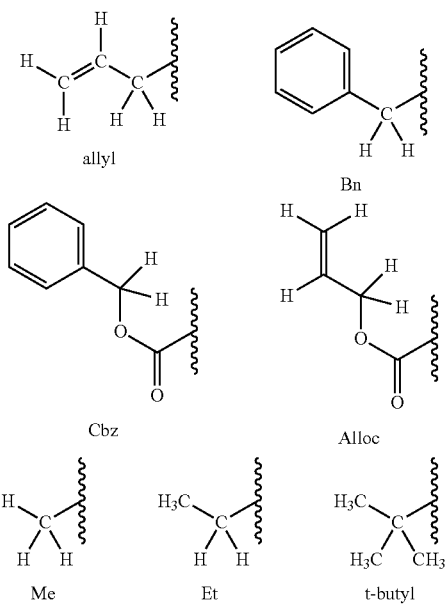

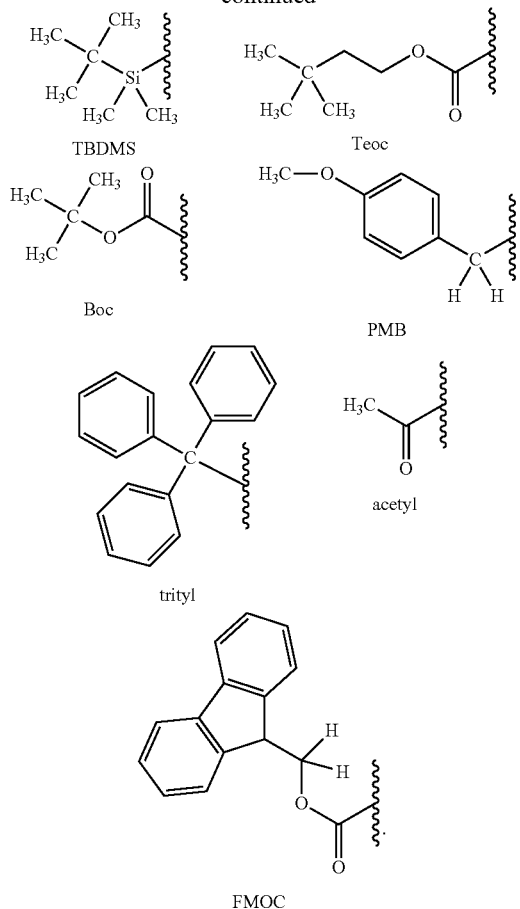

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions of Ubiquitin-Binding Peptides

In various embodiments, the ubiquitin-binding peptides described herein can be conjugated to at least one compound or material that make these conjugate structures useful in analytical applications for the determination of the presence of ubiquitinated substrates. For example, and without limitation, ubiquitin-binding peptides of SEQ ID NO: 1, 2, 4, 5, or 6 can be covalently attached to a dye or a resin. The attachment point of the ubiquitin-binding peptides to the dye or resin can be through a chemical reaction with any suitable reactive atom in Z.

In certain embodiments, a reaction product of a ubiquitin-binding peptide and a resin is provided. The resin comprises, in some embodiments, at least one reactive group that reacts with a sulfhydryl (SH) or selenohydryl (SeH) functionality. The resin can, in some embodiments, comprise an agarose resin. The reactive group on the resin can be, for example, an iodoacetyl group. Other suitable resins include, but are not limited to, polystyrene, polystyrene-PEG composites, PEGylated silica, magnetic beads (agarose or silica based), and PEG and poly-ε-lysine (ε-PL) resins. In certain embodiments, the ubiquitin-binding peptide is conjugated to the resin through an amide, reverse amide, thioamide, ether, ester, thioester, carbonate, carbamate, thiourea, or urea bond in Z.

In some embodiments, a reaction product of a ubiquitin-binding peptide and a dye is provided. The dye can include at least one reactive group that reacts with a sulfhydryl (SH) or selenohydryl (SeH) functionality. In various embodiments, the dye is a cyanine-containing dye such as Cy5. The reactive group is, in some embodiments, a maleimide. Other dyes can be used, depending on the desired type of analysis to be performed. For example, other suitable dyes include coumarin, Cy3, fluorescein, Oregon green, pacific blue, pacific green, PE-Cyanine7, PerCP-Cyanine5.5, tetramethylrhodamine, Texas red, BODIPY dyes, DyLight dyes, Alexafluor dyes, and the like.

Methods of Using Ubiquitin-Binding Peptides

In various embodiments, the methods described herein allow for identification and detection of ubiquitin-bound substrates. The ubiquitin-bound substrate, in some embodiments, is a substrate that is covalently modified and/or bound to at least one ubiquitin. In certain embodiments, the method is also suitable for identification and detection of a substrate that is non-covalently bound or complexed to one or more ubiquitins. The substrates can be mono-ubiquitinated or poly-ubiquitinated. Poly-ubiquitinated substrates can have 2 or more ubiquitins covalently attached to the substrate. In some instances, the identity of the ubiquitinated lysine can be determined by mass spectrometry or by other analytical techniques known to those of skill in the art. In certain embodiments, a method of detecting the presence of a ubiquitinated substance includes contacting a sample comprising at least one ubiquitinated substance with a composition containing at least one ubiquitin-binding peptide of SEQ ID NO: 1, 2, 4, 5, or 6, and detecting in the sample the presence of the ubiquitin-binding peptide bound to the at least one ubiquitinated substance.

The detecting is not particularly limited or restricted as to the apparatus or means of detection, and any suitable detection system used in the art can be utilized. In one embodiment, the detecting includes electrophoresis. In other embodiments, the method includes detecting with far-western blotting. In some embodiments, the method includes a ubiquitin-binding peptide that includes a dye. In some embodiments, the method includes a ubiquitin-binding peptide that includes a resin.

EXAMPLES

Various embodiments of the present application can be better understood by reference to the following Examples which are offered by way of illustration. The scope of the present application is not limited to the Examples given herein.

Example 1. Ubiquitin Proteomics

The feasibility of using the peptide of SEQ ID NO: 2 as a ubiquitin conjugate-enrichment tool was studied. The peptide of SEQ ID NO: 2 was chemically covalently conjugated to a SULFOLINK® resin (Thermo Fisher) to form a peptide of SEQ ID NO: 3 (VVV-Z, wherein Z is a resin containing iodoacetyl groups, and V-Z is a covalent bond between at least one cysteine residue and an X group on the resin). The peptide of SEQ ID NO: 3 was then incubated with yeast (*S. cerevisiae*) lysates followed by a variety of washes (15 columns volumes of: 1. Lysis buffer, 2. TBST, 3. Buffered 1M NaCl, 4. pH 6.0 phosphate buffer) and finally, a series of low-pH glycine elutions.

The peptide of SEQ ID NO: 3 efficiently absorbed ubiquitinated proteins from yeast lysates compared to the negative control resin (FIG. 1, FT). After column binding, the proteins could be extensively and stringently washed (see above) without losing ubiquitinated proteins, due to the high-affinity interaction. Finally, the ubiquitinated proteins readily eluted when exposed to a low-pH glycine buffer that is quickly neutralized in Tris buffer. Elution 2 from the peptide of SEQ ID NO: 3 highlights how well the column could bind ubiquitin as mono-ubiquitin (~10 kDa) and ubiquitin-conjugates (>25 kDa) are readily detectable. The pooled elutions from this experiment were submitted for mass spectrometry analysis.

Assessment of the aforementioned column eluates by tandem mass spectrometry identified 1,503 unique proteins with high confidence across the entire experiment. The peptide of SEQ ID NO: 3 strongly enriched ubiquitin with 540 total spectral counts compared to 13 in the negative control. The 540 total peptides gave ~95% coverage with only the last 4 residues being absent (peptide that would not fly in the MS). To determine if any of the seven lysine-based ubiquitin linkage types had been detected, peptides with an additional mass of 114 Daltons (mass of the residual ubiquitin C-terminal di-glycine left after trypsin cleavage) were investigated. Peptides consistent with all seven lysines on ubiquitin being ubiquitin modified were identified, indicating that lysine-based ubiquitin linkages can be unambiguously enriched.

Figure 2:
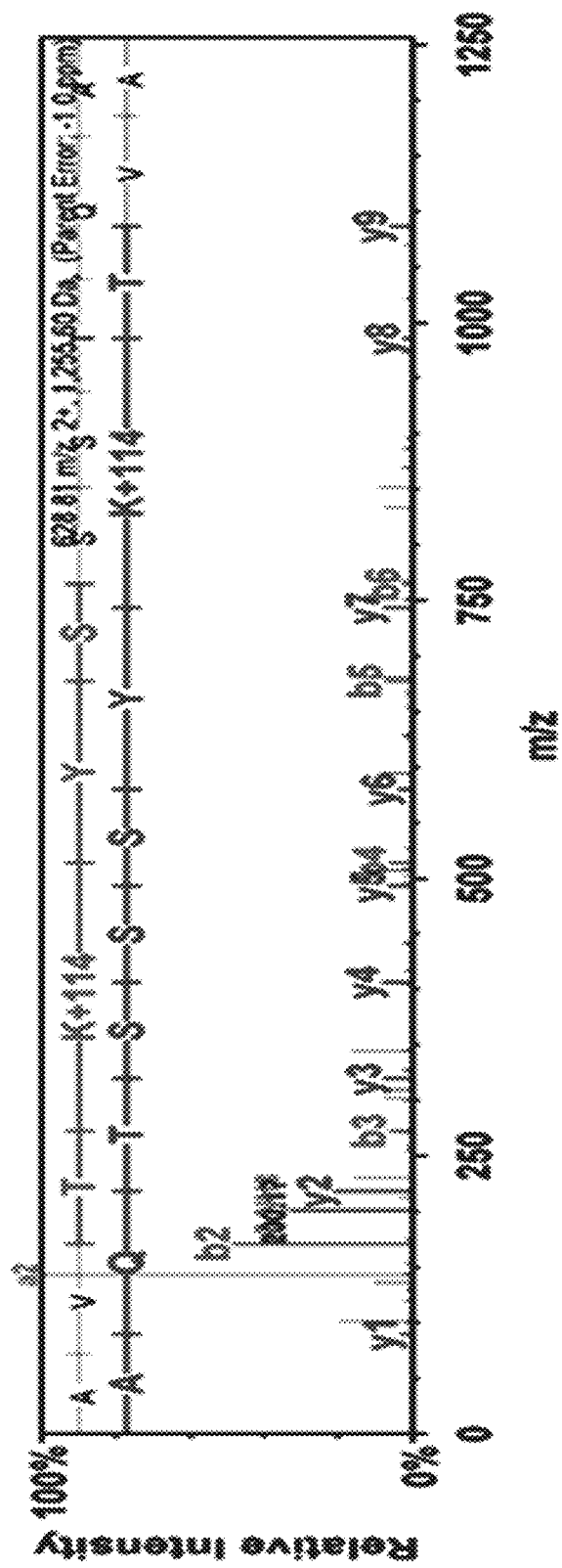
FIG. 2 illustrates the Lys123 di-Gly peptide spectrum of histone H2B peptide (R)AVTkYSSSTQA(−) (residues 121-131). The additional 114 Da was detected by b- and y-ions.

The mass spectrometry data was queried for a subset of known mono-ubiquitinated substrates in yeast: PCNA (Pol30), Epsin-1 (Ent1) and Histone H2B (H2B1). Enrichment of all three proteins in the OtUBD-resin elution was observed compared to control. For Pol30, 7 total spectra were present compared to 0 in the control, covering 44% of the 29 kDa protein. Ent1 had 15% coverage (52 kDa) in 6 spectra compared to 0 in the control. Ten spectra of Histone 2B were obtained compared to 1 in the control. The 10 spectra covered 43% of the protein and included a single di-Gly modified peptide on Lys123 (the residue known to be monoubiquitinated—FIG. 2). The additional di-Gly mass (114 Da) was detected by both b- and y-ions and the lysine is centrally located within the peptide making it a high confidence hit.

Example 2. Ubiquitin Detection

Figure 3:
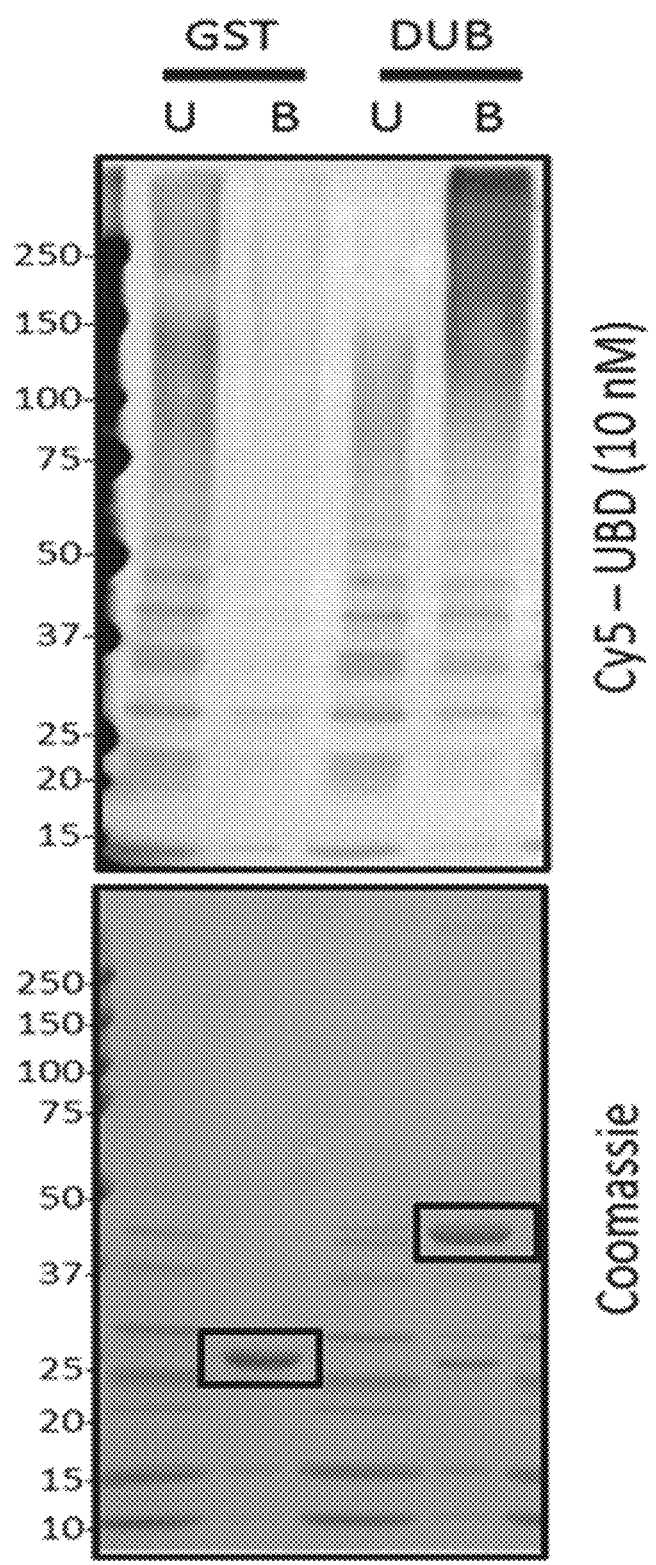
FIG. 3 illustrates ubiquitin detection by Cy5-OtUBD gel overlay. Lys48-linked ubiquitin chains were incubated with GST or GST-OtDUB-C135A and bound to a glutathione resin. Unbound (U) and bound (B) fractions were resolved and detected by Coomassie staining of protein and Cy5-OtUBD labeling of ubiquitinated species. Boxed bands in lanes 2 and 4 are GST and GST-OtDUB, respectively.

The peptide of SEQ ID NO: 2 was conjugated to Cy5-maleimide to form a peptide of SEQ ID NO: 9 (Cy5-OtUBD). Extended Lys48 ubiquitin chains were generated in vitro and a pulldown experiment was performed with GST alone or GST-OtDUB-C135A (an inactive form of a DUB domain in the same polypeptide from which OtUBD is derived, which is known to bind Lys48 chains). Unbound and bound samples were resolved by SDS-PAGE, and Coomassie stained or run in a Far-Western gel overlay with Cy5-labeled OtUBD (FIG. 3). In the Coomassie-stained gel, one can readily detect the bait GST and OtDUB proteins (FIG. 3, boxed) and some poly-ubiquitin ladders. Ubiquitin chains are readily detected by the Cy5-OtUBD.

Example 3. Purification of Cys-UBD

The ubiquitin binding domain (UBD) from *Orientia* DUB was modified and cloned into pRT498 vector (modified pET42b vector). The resultant plasmid codes for the UBD with an N-terminal 6×His-MBP-tag followed by a TEV protease cleavage site and the 3-amino acid sequence CGC or CGG upstream of the UBD. pRT498-cys-OtUBD plasmid was transformed into *E. coli* Rosetta competent cells. The cells were cultured at 37° C. to log phase and induced with 0.3 mM IPTG at 16° C. overnight. The cells were harvested and lysed by a French press in a pH 8.0 50 mM Tris HCl, 300 mM NaCl, 10 mM imidazole buffer supplemented with 2 mM PMSF (phenylmethanesulfonyl fluoride), lysozyme, and DNase I. The lysate was clarified by 1 h centrifugation at 4° C. at 10,000 rcf before being subjected to standard Ni-NTA affinity purification. The purified cys-UBD was concentrated and re-diluted in pH 7.5 50 mM Tris HCl, 150 mM NaCl buffer supplemented with 10 mM TCEP. His-tagged TEV protease was added to cleave the tags and the mixture was incubated on ice overnight. The next day, the cleavage mixture was let flow through a bed of Ni-NTA beads. The flow-through was concentrated and purified by FPLC with a Superdex 75 gel filtration column and pH 7.5 50 mM Tris HCl, 150 mM NaCl buffer supplemented with 2 mM TCEP.

As an alternative way to create the affinity resin, the coding sequence of OtUBD was cloned into the pET21a vector together with coding sequence for an N-terminal cysteine followed by 6×His-tag. The resultant plasmid codes for OtUBD with a single N-terminal cysteine and 6×His-tag. pET21a-cys-6×His-OtUBD plasmid was transformed into *E. coli* Rosetta competent cells. The cells were cultured at 37° C. to log phase and induced with 0.3 mM IPTG at 16° C. overnight. The cells were harvested and lysed by a French press in a pH 8.0 50 mM Tris HCl, 300 mM NaCl, 10 mM imidazole buffer supplemented with 2 mM PMSF, lysozyme and DNase I. The lysate was clarified by 1 h centrifugation at 4° C. at 10,000 rcf before being subjected to standard Ni-NTA affinity purification. To the eluted cys-6×His-UBD was added 5 mM TCEP. The solution was concentrated and purified by FPLC with a Superdex 75 gel filtration column and pH 7.5 50 mM Tris HCl, 150 mM NaCl buffer supplemented with 1 mM TCEP. This method yields higher amounts of protein with a slightly simpler protocol but the first cys-UBD preparation method is useful when a tag-less version of cys-UBD is desired.

Example 4. Conjugation of Cys-UBD to Commercial SULFOLINK® UBD Resin

Sulfo-link UBD resin was made by conjugating cys-UBD to SULFOLINK® resin according to manufacturer's protocol. Briefly, 2 mL bed volume of SULFOLINK® resin was equilibrated with coupling buffer (50 mM Tris, 5 mM EDTA-Na; pH 8.5). Cys-UBD (4 mg) was diluted in 4 mL of coupling buffer supplemented with 20 mM TCEP (tris(2-carboxyethyl)phosphine) and incubated at room temperature for 30 minutes. The diluted cys-UBD was loaded to the sulfo-link resin and the mixture was incubated at room temperature for 30 minutes with rotation. The resin was allowed to settle for another 30 minutes before drained and washed with 6 mL coupling buffer. L-cysteine (4 mL, 50 mM) dissolved in coupling buffer was added to the resin and the mixture was incubated at room temperature for 30 minutes with rotation. The resin was allowed to settle for another 30 minutes before drained and washed with 12 mL 1 M NaCl followed by 4 mL column buffer (50 mM Tris HCl, 150 mM NaCl, 1 mM EDTA, 0.5% Triton-X, 10% glycerol, pH 7.5). To make the negative control resin, 50 mM cysteine was directly added to pre-washed sulfo-link resin followed by the same wash steps mentioned above. The resins were stored in column buffer supplemented with 0.05% sodium azide at 4° C. until use.

Example 5. Ability of OtUBD to Protect Bulk Mono- and Polyubiquitylated Species Ubiquitin-protein conjugates are subject to rapid deconjugation in vitro, often hampering the ability to identify ubiquitylated species. TUBE (tandem ubiquitin binding entity) proteins have been used as a way to prevent this, but they only have high affinity for polyubiquitylated proteins and not monoubiquitylated ones. The ability of OtUBD to protect bulk ubiquitylated species in yeast whole cell lysate as well as monoubiquitylated histone H2B with a TUBE derived from the UBA domain of UBQLN1 [4xTR-TUBE, expression plasmid obtained from Addgene (ID: 110312); reference: Tsuchiya et al Nat Commun. 2018 Feb. 6; 9(1): 524. doi: 10.1038/s41467-018-02869-x.]. Yeast ubp8/1 cells expressing Flag-tagged histone H2B were harvested during log phase growth and lysed by grinding in liquid nitrogen.

Protein was extracted with lysis buffer (50 mM Tris HCl, 150 mL NaCl, 1 mM EDTA, 10% glycerol, protease inhibitor cocktail, 1 mM PSMF) supplemented with 20 mM NEM, 3 µM UBD, 3 µM TUBE (all final concentrations), or nothing. The resulting lysates were cleared by centrifugation, incubated at room temperature 1-4 hours, and subjected to anti-Flag immunoprecipitation. The whole cell lysates were resolved on SDS-PAGE and immunoblotted for ubiquitin. The Flag-antibody precipitated fractions were resolved on SDS-PAGE and immunoblotted with anti-Flag antibody. As shown in FIG. 4A, just like NEM, a general cysteine protease inhibitor, both OtUBD and the TUBE were able to protect bulk ubiquitylated species in the whole cell lysate from deubiquitylation (darker smear of bands compared to no additive ("–") lane) to a comparable extent. Surprisingly, only OtUBD—but not the TUBE—was able to protect mono-ubiquitylated Flag-H2B.

In FIG. 4A, yeasts with ubp8Δ and Flag-tagged histone H2B were harvested during log phase growth and lysed by grinding in liquid nitrogen. Whole cell protein was extracted with lysis buffer (50 mM Tris HCl, 150 mL NaCl, 1 mM EDTA, 10% glycerol, protease inhibitor cocktail, 1 mM PSMF) supplemented with the indicated additives (none; 20 mM NEM, 3 µM UBD or 3 µM TUBE). The resulted lysates were cleared by centrifugation, incubated at room temperature for the indicated time and subjected to Flag pulldown. The whole cell lysates were resolved on SDS-PAGE and immunoblotted for ubiquitin. The Flag-antibody precipitated fractions were resolved on SDS-PAGE and immunoblotted with anti-Flag antibody. The whole cell lysates resolved on SDS-PAGE were also Ponceau stained to assess loading.

In another example, WT or bre1Δ yeast expressing Flag-tagged histone H2B were harvested during log phase growth. Whole cell extracts were made by bead beating in the presence of trichloroacetic acid and dissolving the resultant pellet with SDS gel-loading buffer to extract chromatin. UBD pulldown (as described in Example 6 herein) was performed with whole cell extracts diluted with buffer lacking SDS. As shown in FIG. 4B, UBD resin was surprisingly able to enrich for monoubiquitylated Flag-H2B even when its level in the whole cell lysate was too low to be detected by immunoblotting. These examples demonstrate OtUBD's unexpected ability to bind tightly to mono-ubiquitylated proteins. In various embodiments, OtUDB can be useful as a tool to protect and enrich both mono-ubiquitylated and polyubiquitylated proteins.

In FIG. 4B, WT or bre1Δ yeasts expressing Flag-tagged histone H2B were harvested during log phase growth. Whole cell extracts were made by bead beating in the presence of TCA and dissolving the resultant pellet with SDS buffer to extract chromatin. UBD pulldown (as described earlier) was performed with whole cell extracts diluted with buffer without SDS. Input (IN), flow-through (FT) and eluted fraction (E) from the Flag UBD pulldown were resolved on SDS-PAGE and immunoblotted with anti-Flag antibody.

Example 6. Pulldown and Mass Spectrometry with Sulfo-Link UBD Resin

Pull-down of ubiquitin-containing targets and their subsequent mass spectrometric analysis was conducted under the following conditions:
Pull-Down Conditions
  Column buffer: 50 mM Tris HCl, 150 mM NaCl, 1 mM EDTA, 0.5% Triton-X, 10% glycerol, pH 7.5
  Lysis buffer: 50 mM Tris HCl, 150 mM NaCl, 1 mM EDTA, 0.5% Triton-X, 10% glycerol, 20 uM MG132, 30 mM NEM, cOmplete mini (EDTA-free), 2 mM PSMF, pH7.5
  Wash buffer 1: 50 mM Tris HCl, 150 mM NaCl, 0.1% Tween 20, pH 7.5
  Wash buffer 2: 50 mM Tris HCl, 1M NaCl, pH 7.5
  Wash buffer 3: 50 mM sodium phosphate buffer, 100 mM NaCl, pH 6.0
  Elution buffer 1: 100 mM Glycine, pH 3 (pH adjusted with HCl)
  Elution buffer 2: 100 mM Glycine, pH 2.5 (pH adjusted with HCl)
  Neutralization buffer: 1 M Tris HCl, pH 8.8
Mass Spectrometry and Pull-Down
  1. Frozen yeast powder was extracted with yeast lysis buffer (1:1 v/v) on ice with intermittent Vortexing for 10 min.
  2. The crude extract was centrifuged at 21,000 rcf either with a floor centrifuge or a table top mini centrifuge for 15 min.
  3. The supernatant was carefully transferred to a clean tube. The protein concentration was determined with BCA assay. The supernatant was diluted to 4 mg/mL with lysis buffer.
  4. Sulfo-link-UBD resin or Sulfo-link resin capped with cysteine was transferred to a plastic column. Typically, 2 mL bed volume of resin was used for 100 mg of lysate. The storage buffer was drained. All pulldown procedures were carried out at 4° C.
  5. 5 CV column buffer was used to equilibrate the resin.
  6. The bottom of the column was capped. 12 CV of 4 mg/mL yeast lysate was mixed with the resin in the column.
  7. The mixture was incubated with rotation for 2 hours.
  8. The column was allowed to settle and the liquid drained.
  9. The resin was washed with 15 CV of column buffer, followed by 15 CV of wash buffer 1, 15 CV of wash buffer 2 and 15 CV of wash buffer 3.
  10. The bottom of the column was capped. 3 CV of elution buffer 1 was mixed with the resin in the column. The mixture was incubated with rotation for 5 min. The eluate was collected and neutralized immediately with 0.3 CV of 1 M Tris pH 8.8.
  11. The bottom of the column was capped. 3 CV of elution buffer 2 was mixed with the resin in the column. The mixture was incubated with rotation for 5 min. The eluate was collected and neutralized immediately with 0.3 CV of 1 M Tris pH 8.8.
  12. Step 11 was repeated one time.
  13. The eluates were flash frozen with liquid nitrogen and freeze-dried in a lyophilizer.
  14. The lyophilized eluates were reconstituted in water, cleaned up by acetone precipitation and methanol chloroform extraction.
  15. The resulted proteins were alkylated and digested by trypsin before subjected to LC-MS/MS analysis.

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

ENUMERATED EMBODIMENTS

The following enumerated embodiments are provided, the numbering of which is not to be construed as designating levels of importance.

Embodiment 1 provides an ubiquitin-binding peptide comprising the sequence of SEQ ID NO: 1 or SEQ ID NO:5, wherein Z is $(X_{aa})_n$ or L; wherein each $X_{aa}$ is independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, penicillamine, homocysteine, and selenomethionine; provided that at least one $X_{aa}$ is selected from the group consisting of cysteine, selenocysteine, penicillamine, homocysteine, methionine, and selenomethionine; wherein L is a chemical moiety comprising from 1 to 500 atoms selected from the group consisting of C, N, O, S, P, H, F, Cl, and Br; and wherein n is an integer from 1 to 1000.

Embodiment 2 provides the peptide of Embodiment 1, wherein Z is $(X_{aa})_n$.

Embodiment 3 provides the peptide of any of embodiments 1-2, wherein n is 6.

Embodiment 4 provides the peptide of any of embodiments 1-3, wherein at least one $X_{aa}$ is cysteine.

Embodiment 5 provides the peptide of any of embodiments 1-4, wherein at least two $X_{aa}$ are independently cysteine.

Embodiment 6 provides the peptide of any of embodiments 1-5, wherein Z has the sequence of SEQ ID NO: 3.

Embodiment 7 provides the peptide of any of embodiments 1-6, wherein the peptide has the sequence of SEQ ID NO: 4.

Embodiment 8 provides the peptide of any of embodiments 1-7, wherein the peptide has the sequence of SEQ ID NO: 6.

Embodiment 9 provides a reaction product of the peptide of any one of embodiments 1-8 and a resin, wherein the resin comprises at least one reactive group that can react with a sulfhydryl (SH) or selenohydryl (SeH) functionality.

Embodiment 10 provides the reaction product of embodiment 9, wherein the resin comprises agarose.

Embodiment 11 provides the reaction product of any of embodiments 9-10, wherein the at least one reactive group is an iodoacetyl group.

Embodiment 12 provides the reaction product of the peptide of any of embodiments 1-8 and a dye, wherein the dye comprises at least one reactive group that can react with a sulfhydryl (SH) or selenohydryl (SeH) functionality.

Embodiment 13 provides the reaction product of embodiment 12, wherein the dye comprises cyanine.

Embodiment 14 provides the reaction product of any of embodiments 12-13, wherein the reactive group is a maleimide.

Embodiment 15 provides a method of detecting the presence of a ubiquitinated substance, the method comprising: contacting a sample comprising at least one ubiquitinated substance with the peptide of any of embodiments 1-8, and detecting in the sample the presence of the ubiquitin-binding peptide bound to the at least one ubiquitinated substance.

Embodiment 16 provides the method of embodiment 15, wherein the detecting comprises electrophoresis.

Embodiment 17 provides the method of any of embodiments 15-16, wherein the detecting comprises far-western blotting.

Embodiment 18 provides the method of any of embodiments 15-17, wherein the ubiquitin-binding peptide comprises a dye.

Embodiment 19 provides the method of any of embodiments 15-18, wherein the ubiquitin-binding peptide comprises a resin.

What is claimed is:

1. An ubiquitin-binding peptide having the sequence of SEQ ID NO: 1 or SEQ ID NO: 5,
wherein Z is a sequence of amino acids or amino acid analogs having the sequence $(X_{aa})_n$ or Z is L;
wherein n is 6;
wherein each $X_{aa}$ is independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, penicillamine, homocysteine, and selenomethionine;
provided that at least one $X_{aa}$ is selected from the group consisting of cysteine, selenocysteine, penicillamine, homocysteine, methionine, and selenomethionine;
wherein L is a chemical moiety selected from the group consisting of beta-alanine, 4-aminobutyric acid, 2-aminoethoxyl acetic acid, 5-aminovaleric acid, 6-aminohexanoic acid, 8-amino-3,6-dioxaoctanoic acid, 12-amino-4,7,10-trioxadodecanoic acid, 15-amino-4,7,10,13-tetraoxapenta-decanoic acid, trioxatridecan-succinamic acid, 11-azido-3,6,9-trioxaundecanoic acid, 2-[2-(2-propyn-1-yloxy)ethoxy]ethanoic acid, and 4,7,10,13,16-pentaoxanonadecanedioic acid di(N-succinimidyl)ester.

2. The peptide of claim 1, wherein Z is $(X_{aa})_n$.

3. The peptide of claim 1, wherein at least one $X_{aa}$ is cysteine.

4. The peptide of claim 1, wherein at least two $X_{aa}$ are cysteine.

5. The peptide of claim 2, wherein Z has the sequence of SEQ ID NO: 3.

6. The peptide of claim 5, wherein the peptide has the sequence of SEQ ID NO: 4.

7. The peptide of claim 5, wherein the peptide has the sequence of SEQ ID NO: 6.

8. A reaction product of the peptide of claim 1 and a resin, wherein the resin comprises at least one reactive group that can react with a sulfhydryl (SH) or selenohydryl (SeH) functionality.

9. The reaction product of claim 8, wherein the resin comprises agarose.

10. The reaction product of claim 8, wherein the at least one reactive group is an iodoacetyl group.

11. A reaction product of the peptide of claim 1 and a dye, wherein the dye comprises at least one reactive group that can react with a sulfhydryl (SH) or selenohydryl (SeH) functionality.

12. The reaction product of claim 11, wherein the dye comprises cyanine.

13. The reaction product of claim 11, wherein the reactive group is a maleimide.

14. A method of detecting the presence of a ubiquitinated substance, the method comprising:
contacting a sample comprising at least one ubiquitinated substance with the peptide of claim 1; and
detecting in the sample the presence of the ubiquitin-binding peptide bound to the at least one ubiquitinated substance.

15. The method of claim 14, wherein the detecting comprises electrophoresis.

16. The method of claim 14, wherein the detecting comprises far-western blotting.

17. The method of claim 14, wherein the ubiquitin-binding peptide comprises a dye.

18. The method of claim 14, wherein the ubiquitin-binding peptide comprises a resin.

* * * * *